United States Patent [19]
Jewell

[11] Patent Number: 5,631,166
[45] Date of Patent: May 20, 1997

[54] SPECIMEN DISK FOR BLOOD ANALYSES

[76] Inventor: Charles R. Jewell, 9810 Kingsbridge Dr., #102, Fairfax, Va. 22031

[21] Appl. No.: 407,630

[22] Filed: Mar. 21, 1995

[51] Int. Cl.$^6$ ................................................ G01N 21/07
[52] U.S. Cl. .................. 436/45; 422/72; 422/102; 422/104; 436/165
[58] Field of Search ................... 210/94, 198.1, 210/209, 232, 782, 787; 422/72, 102, 104; 435/288.3, 288.4, 288.5, 305.1, 305.2, 305.3, 305.4; 436/45, 177, 165; 494/10

[56] References Cited

U.S. PATENT DOCUMENTS

| | | | |
|---|---|---|---|
| 3,533,744 | 10/1970 | Unger . | |
| 3,586,484 | 6/1971 | Anderson | 356/39 |
| 3,617,222 | 11/1971 | Matte | 356/39 |
| 3,681,029 | 8/1972 | Shapiro | 356/39 |
| 3,744,975 | 7/1973 | Mailen | 422/72 |
| 3,759,666 | 9/1973 | Hill, Jr. | 436/45 |
| 3,864,089 | 2/1975 | Tiffany et al. | 422/72 |
| 3,873,217 | 3/1975 | Anderson et al. | 422/72 |
| 4,097,845 | 6/1978 | Bacus | 356/39 |
| 4,202,037 | 5/1980 | Glaser et al. | 356/39 |
| 4,519,087 | 5/1985 | Deindoerfer | 356/39 |
| 4,656,083 | 4/1987 | Hoffmann et al. | 428/265 |
| 4,700,298 | 10/1987 | Palcic et al. | 356/39 |
| 4,727,033 | 2/1988 | Hijikata et al. | 356/39 |
| 4,741,043 | 4/1988 | Bacus | 356/39 |
| 4,761,075 | 8/1988 | Matsushita et al. | 356/39 |
| 4,770,779 | 9/1988 | Ichikawa et al. | 210/561 |
| 4,837,160 | 6/1989 | Meserol et al. | 356/39 |
| 4,847,205 | 7/1989 | Burtis et al. | 422/72 |
| 4,902,479 | 2/1990 | Bri kus | 422/72 |
| 5,061,381 | 10/1991 | Burd | 210/789 |
| 5,098,845 | 3/1992 | Babson | 436/45 |
| 5,116,765 | 5/1992 | Watanabe et al. | 356/39 |
| 5,149,501 | 9/1992 | Babson et al. | 422/58 |
| 5,186,709 | 2/1993 | Hissung | 422/72 |
| 5,218,645 | 6/1993 | Bacus | 364/413.08 |
| 5,235,522 | 8/1993 | Bacus | 364/413.1 |
| 5,242,803 | 9/1993 | Burtis et al. | 422/72 |
| 5,246,666 | 9/1993 | Vogler et al. | 422/73 |
| 5,256,376 | 10/1993 | Callan et al. | 422/72 |

OTHER PUBLICATIONS

R&M Biometrics, Inc./BIOQUANT, "BQ Meg IV – Scientific Image Analysis System", pp. 1–6. (undated).

Biohit Proline® Electronic Pipettor, "The Ultimate Pipetting Experience", pp. 1–9 (undated).

*Primary Examiner*—John Kim
*Attorney, Agent, or Firm*—Hazel & Thomas, P.C.

[57] ABSTRACT

A disk for holding, centrifuging and microscopically viewing fluid samples is provided. The disk includes a plurality of reaction wells radiating outwardly and includes a barrier to restrain particles during centrifugation. This disk is used in the disclosed apparatus and method for blood typing and related procedures. The apparatus comprises sample loading, mixing, centrifuging, incubating, viewing and sterilizing stations. Additionally, a photomicrograph of the sample is taken, digitized, displayed, stored and printed along with corresponding test results and interpretation.

6 Claims, 4 Drawing Sheets

SPECIMEN DISK FOR BLOOD ANALYSES

BACKGROUND OF THE INVENTION

1. Field of the Invention

The present invention relates generally to hemo-analysis. More particularly, the invention relates to a testing disk for handling and carrying samples and also to a method and apparatus for analyzing, storing, displaying and printing data from blood typing and other related procedures.

2. Description of the Prior Art

Blood grouping is a routine procedure for categorizing human blood into one of four classifications: A, B, AB or O. Currently, blood grouping is accomplished by inducing agglutination, i.e., clumping, in red blood cell suspensions. To perform this procedure a patient's blood sample is clotted and then centrifuged to separate the red blood cells from the blood serum. A small amount of red blood cells is mixed with a diluent and a portion of this test solution is introduced into a test tube. The test tube also contains either anti-A-serum, anti-B-serum or anti-AB-serum. At various stages of the procedure, reagents facilitating and enhancing immunological reactions are added to the test solution and the resulting solution is incubated, centrifuged and agitated. A sample is then removed from the solution and visually analyzed under a microscope to determine whether cell agglutination has occurred.

A sample which agglutinates in the presence of anti-A reagent, but does not agglutinate with the presence of anti-B reagent is identified as blood type A. Similarly, a sample which agglutinates with anti-B reagent but does not agglutinate with anti-A reagent is classified as blood type B. A sample which agglutinates with both anti-A and anti-B reagents is classified as blood type AB, and a sample which does not respond to either reagent is classified as blood type O.

Presently, a variety of factors combine to make blood grouping procedures costly, error prone, slow to complete and potentially dangerous to technicians completing the procedures. For example, blood grouping procedures are usually performed manually by a trained technician. The technician subjectively evaluates the procedure's results and, consequently, blood grouping procedures are slow, labor intensive and error prone. Because of the subjective nature of sample evaluation, results from these tests are far from uniform. Such factors as the technician's experience, training and fatigue strongly influence the technician's evaluation of the sample. Unfortunately, the consequences of an error can be fatal.

Blood grouping procedures also require the use of a variety of glass objects, including microscope slides, cover slips and pipettes. These glass objects are non-reusable, must be discarded after use and are hazardous if cracked or shattered. Furthermore, the glass objects are contaminated with potentially dangerous human blood and special care must be exercised for proper and safe disposal. Glass object disposal and replacement results in unwanted and unnecessary expense for performing blood grouping procedures.

Additionally, the biological fluid to be tested is usually mixed with other fluids, incubated, centrifuged and microscopically examined. During all stages of the immuno-analyses procedure the technician is routinely exposed to human blood potentially carrying infectious and possibly lethal diseases. In order to minimize handling and reduce exposure to fragile glass objects, it is desirable to perform the entire analyses using only one sample holder.

Currently, several models of sample holders attempt to reduce blood sample handling during blood grouping and other related procedures. In general, current sample holders are designed to facilitate blood sample centrifuging and separations. Generally, such sample holders are disk-shaped and employ contoured chambers and passages to promote sample mixing and separation. Biological fluids placed within these disks are mixed and separated by being centrifugally forced over chamber walls or through a variety of passages. These disk designs generally do not allow sample testing or microscopic analysis while the sample is held in the disk. Consequently, a need exists for a sample holder to aid sample preparation, handling and microscopic analysis.

Additionally, as discussed above, blood grouping and other immunological tests are generally labor-intensive and error-prone. In order to reduce manual sample handling and increase testing reliability, it is desirable to integrate a sample holder into a fully-automated analysis system. Current analysis systems generally perform immuno-analyses in one of two ways.

The first type of analysis system examines physical characteristics of mounted and stained blood specimens. In general, the specimens are mounted on glass slides and stained with compounds which enhance identification of cells or physical objects within the cells based upon recognizable physical characteristics. These physical characteristics may then be measured, enhanced and tentatively identified. Many of these systems create digitized images of the examined cells and objects, store and manipulate the acquired data and then print a permanent record of testing and analyses results.

The second type of analysis system determines the presence of immunological responses within the specimen. In general, blood samples are mixed and reacted with other substances within the analysis system. If the particles within the sample agglutinate, the solution generally becomes turbid and the specimen's optical density increases and may be measured photometrically. The degree of turbidity depends upon the degree of agglutination and is measured photometrically. The measured data is then processed to determine the extent of agglutination in the sample. In contrast to the first type of analysis systems, this type of analysis system cannot create digitized images of cells or cell features.

Thus, the prior art has been described with reference to blood grouping. However, the same limitations of utilizing manual procedures evident with blood grouping apply to other blood analysis procedures such as, for example, Rh typing, anti-body screening, anti-body identification and donor/recipient compatibility cross matching.

As is evident from the above discussion, the analysis systems which microscopically examine physical characteristics of specimen cells do not analyze immunological reactions. In contrast, analysis systems which focus on immunological reactions do not microscopically examine physical characteristics of specimen cells. As a result, a need exists for an automated system integrating a useful sample holder which also analyzes immunological reactions including creating, storing and printing digitized images of immunological responses.

SUMMARY OF THE INVENTION

It is therefore an object of the present invention to provide a sample holding disk for use in automated immuno-assay systems wherein the sample and any reagents may be mixed, centrifuged and microscopically viewed while located in the sample holding disk.

It is yet another broad object to provide an analyzing apparatus for immunological agglutination reactions which can perform immunological analyses and display, store and print images of microscopic and macroscopic objects and other information summarizing immunoassay test results.

In all of the above embodiments, it is an object to provide an analyzing apparatus for identifying human blood types and groups and performing any other human or animal immuno-analysis.

Other objects and features of the present invention will be apparent from the following detailed description of the preferred embodiment.

BRIEF DESCRIPTION OF THE DRAWINGS

The invention will be further described in conjunction with the accompanying drawings, in which.

DETAILED DESCRIPTION OF THE PREFERRED EMBODIMENT

Figure 1:
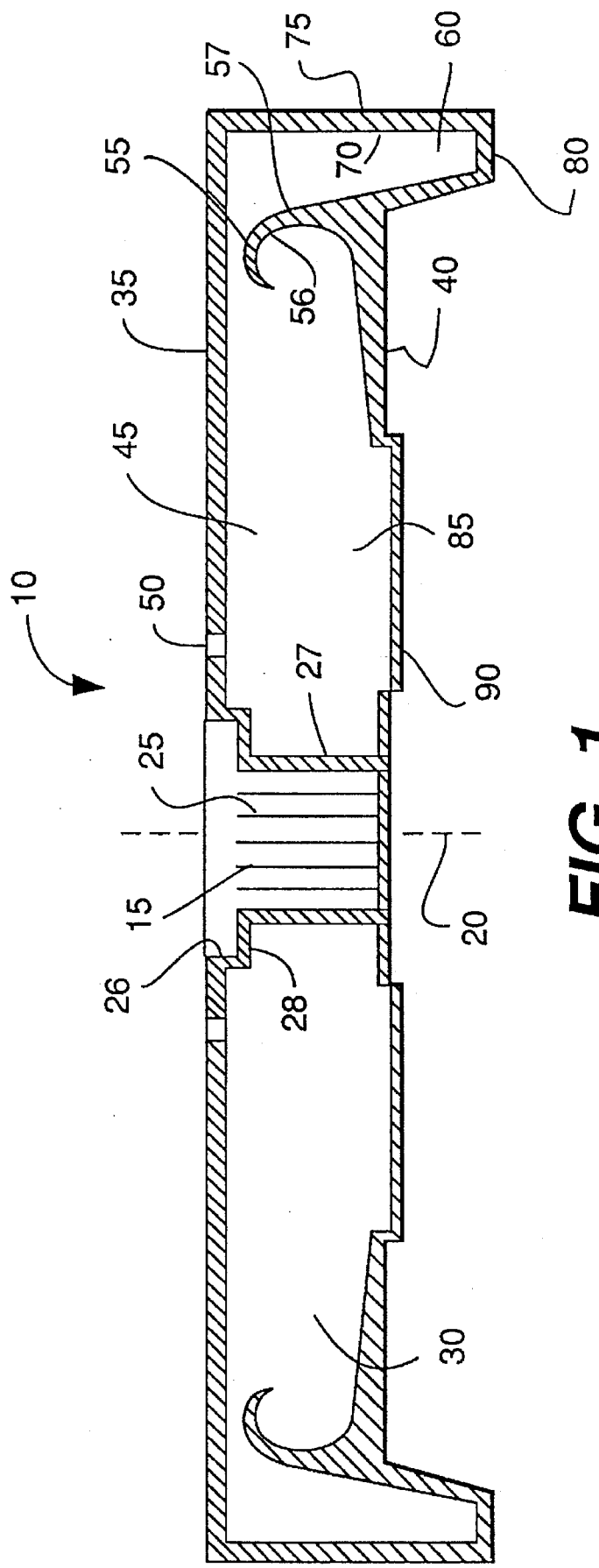
FIG. 1 is a cross-sectional view of a testing disk constructed in accordance with a preferred embodiment of the invention.
Figure 2:
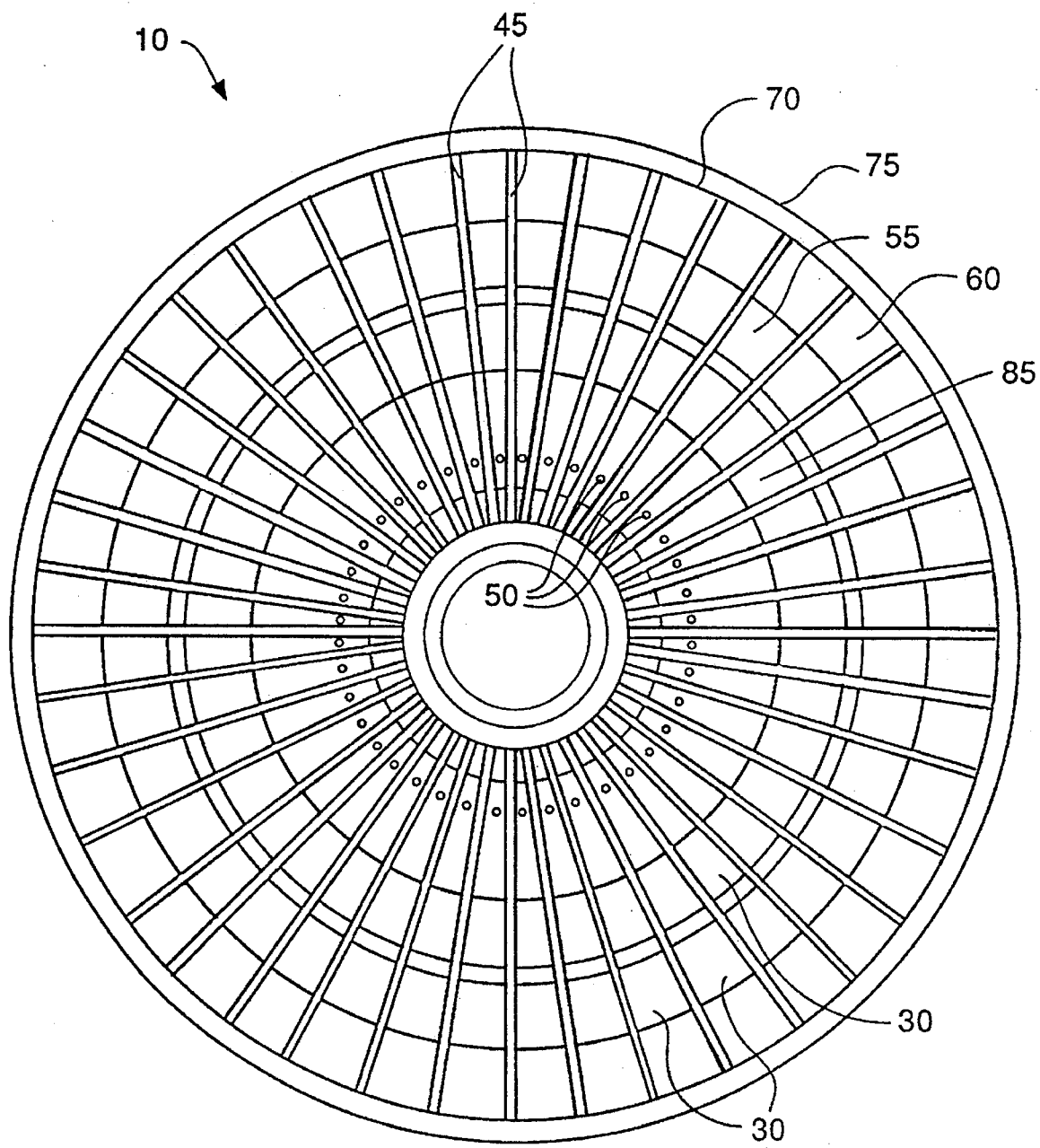
FIG. 2 is an elevational view of a testing disk constructed in accordance with a preferred embodiment of the invention.
Figure 3:
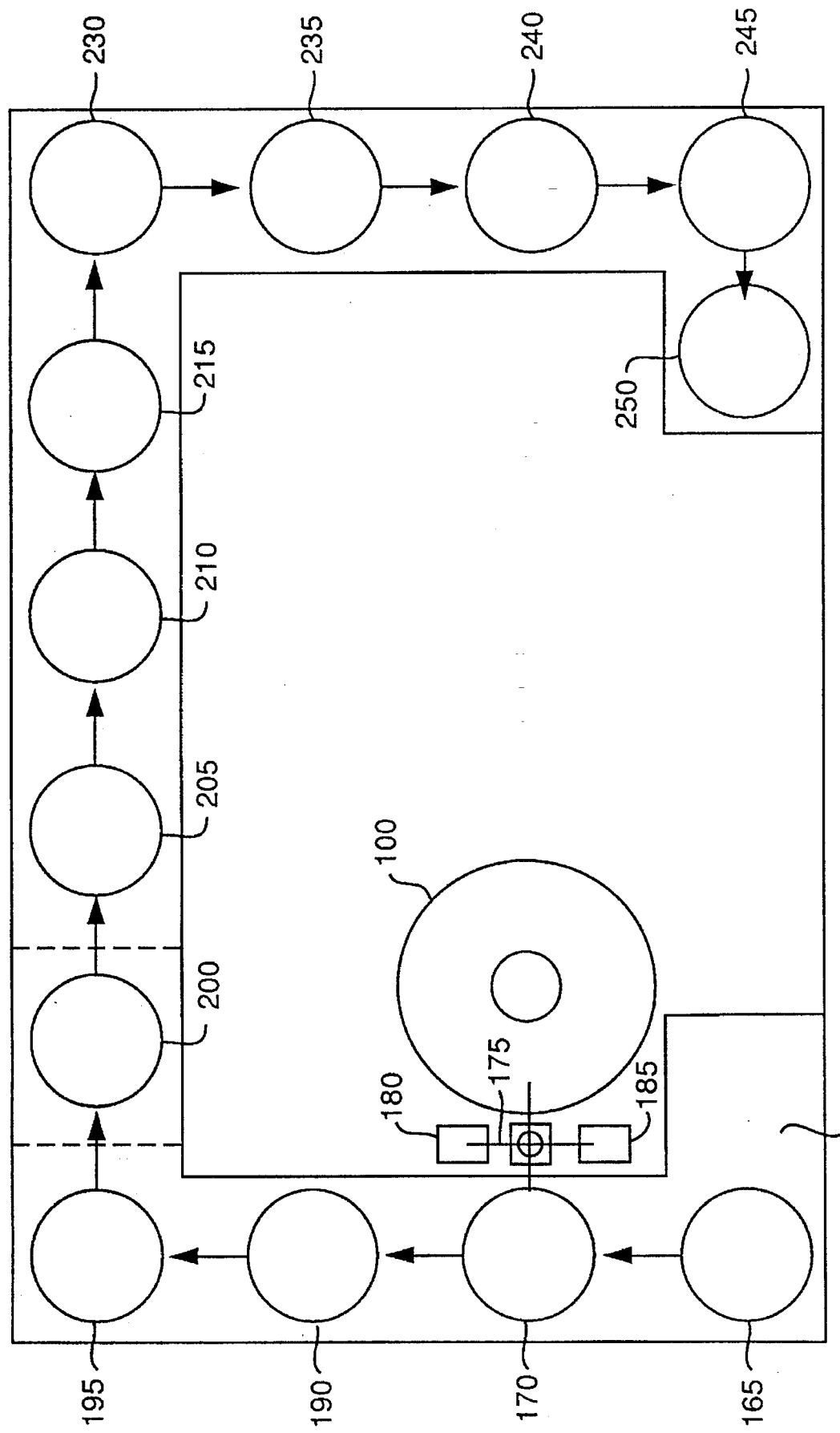
FIG. 3 is a schematic diagram constructed in accordance with a preferred embodiment of the invention, explaining successive steps of an agglutination reaction and evaluation.

With reference to the figures, wherein like reference characters indicate like elements throughout the several views and, in particular, with reference to FIGS. 1 and 2, a specimen disk 10 is illustrated. Specimen disk 10 is circular in shape and contains a centrally located bore 15 along an axis 20. Bore 15 is formed into a T-shaped cross section having a first cylindrical wall 26 of greater diameter than a second cylindrical wall 27 and integrally connected thereto by a substantially horizontal portion 28. Cylindrical wall 27 has a plurality of splines 25 formed thereon and adapted to fit into radial ribs (not shown) of a conveyor mechanism (not shown) for movement through sample processing stations 165 through 250 (FIG. 3). Splines 25 ensure specimen disk 10 is securely held and accurately positioned while engaged with the conveyor mechanism (not shown) when moved into the sample processing stations 165 through 250 (FIG. 3).

A plurality of reaction wells 30 radiate outwardly from the center of specimen disk 10 and are bounded by a reaction well covering 35, a reaction well bottom 40 and two reaction well sides 45. Reaction well covering 35, reaction well bottom 40 and reaction well sides 45 are constructed of a rigid material, preferably polystyrene. Additionally, reaction well covering 35 includes a plurality of covering holes 50 parallel to axis 20 through which testing fluids are injected into each reaction well 30.

Located in each reaction well 30 is a sample centrifugation barrier 55 used to trap particulates during centrifugation. Sample centrifugation barrier 55 includes an inner surface 56 and an outer surface 57. Located near the periphery of each reaction well 30 is a waste chamber 60 bounded by outer surface 57 of sample centrifugation barrier 55, an inner surface 70 of exterior wall 75, reaction well covering 35 and a waste chamber bottom 80 extending below reaction well bottom 40. Inner surface 56 curves upwardly and inwardly in a generally C-shape toward the centerline 20 so as to facilitate dislodgement of compacted matter.

A viewing area 85 is located in reaction well bottom 40 to facilitate microscopic or colorimetric analysis of the contents (not shown) of reaction well 30. In order to facilitate microscopic viewing, bottom viewing surface 90 of viewing area 85 extends below reaction well bottom 40. Bottom viewing surface 90 is constructed of polystyrene or other optically clear material.

In practice, specimens and other fluids (not shown) are introduced into each reaction well 30 through each covering hole 50. Following the introduction of specimens or other fluids, specimen disk 10 may be rotated about axis 20 to centrifugally force relatively heavy matter in the testing fluids against each inner surface 56 of sample centrifugation barrier 55. Relatively heavy material suspended in the specimen becomes compacted against inner surface 56, an excess portion of remaining fluid is centrifugally forced into each waste chamber 60, and a remaining portion of fluid, sufficient to suspend the compacted heavy matter in each viewing area 85, remains in each reaction well 30.

The preferred embodiment of specimen disk 10 contains about forty (40) reaction wells 30, although in practice them may be any other number. Additionally, sample centrifugation barrier 55 employs a C-shaped cross-sectional area to facilitate dislodgement of compacted matter from inner surface 56. Alternatively, or in addition inner surface 56 may be coated with a material to which the relatively heavy matter does not strongly adhere or may be formed into a geometry or surface texture that allows compacted matter to be readily dislodged. The material for coating the inner surface 56, as well as the geometry or surface texture that may be formed on the inner surface 56, are consistent with those materials, geometries and surface textures known in the art for preventing the adherence of compacted material to a surface, such as those shown in U.S. Pat. No. 5,246,666 to Vogler et al., U.S. Pat. No. 4,656,083 to Hoffman et al., and U.S. Pat. No. 4,770,779 to Ichikawa et al.

With reference to FIG. 3, an apparatus for immuno-assays is illustrated. A blood specimen sample is prepared for hemo-analysis by separating the whole blood into blood serum and blood cells. These solutions, and a donor cell suspension against which the patient's sample will be tested, are manually loaded into a specimen carousel 100 by known methods.

Figure 4:
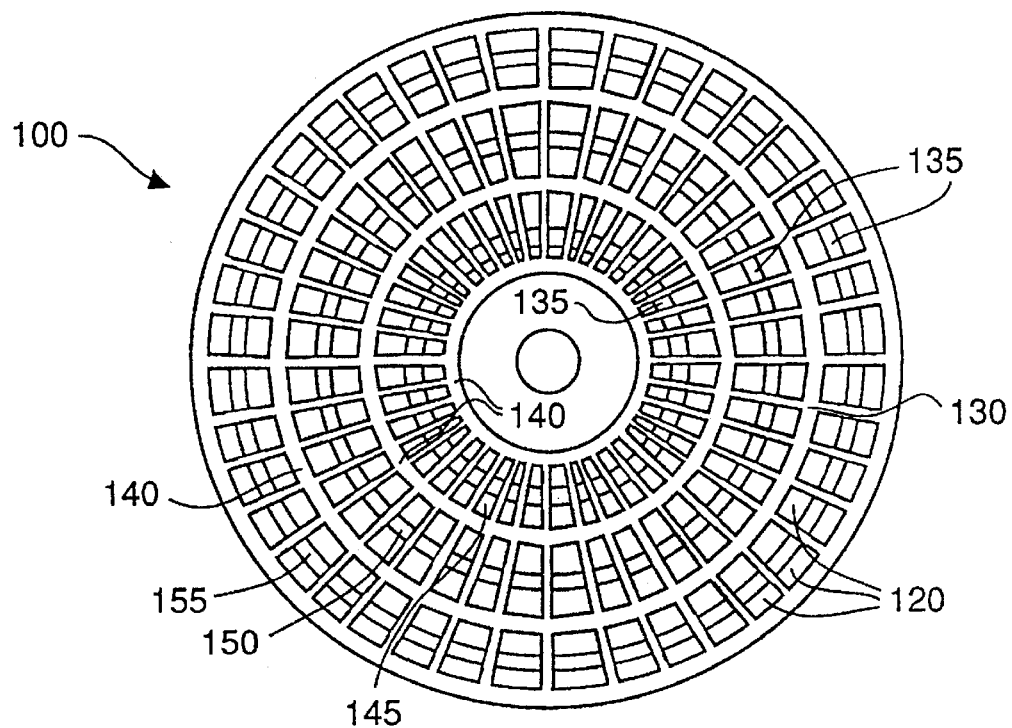
FIG. 4 is an elevational view of a specimen carousel constructed in accordance with a preferred embodiment of the invention.
Figure 5:
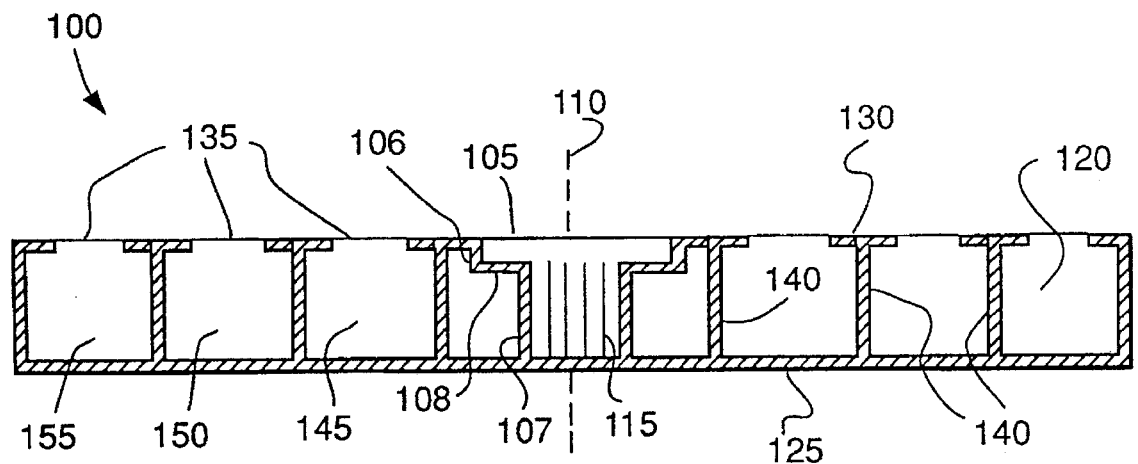
FIG. 5 is a cross-sectional view of a specimen carousel constructed in accordance with a preferred embodiment of the invention.

With reference to FIGS. 4 and 5, specimen carousel 100 is circular in shape with a centrally-located bore 105 along an axis 110. Bore 105 is formed into a T-shaped in cross section having a first cylindrical wall 106 of greater diameter than a second cylindrical wall 107 and integrally connected thereto by a substantially horizontal portion 108. Cylindrical wall 107 has a plurality of splines 115 formed thereon and adapted to fit into radial ribs of a central hub mechanism (not shown). Splines 115 facilitate accurate indexing by successively aligning specimen carousel 100 in a well-defined angular position.

Specimen carousel 100 contains a plurality of specimen wells 120 radiating outwardly from the center of specimen carousel 100. There may be any number of specimen wells 120 but the preferred embodiment contains a number equal to the number of reaction wells in specimen disk 10.

With reference to FIG. 5, specimen carousel 100 includes a solid bottom surface 125 and carousel cover 130 with pipettor holes 135 allowing the introduction and withdrawal of testing solutions (not shown). Each specimen well 120 is divided into three chambers by divider walls 140 (FIG. 4). Inner well 145 holds blood serum from the patient to be tested, middle well 150 holds blood cells from the patient to be tested and outer well 155 holds a donor cell suspension against which the patient's sample is tested. Solid bottom surface 125, carousel cover 130 and divider walls 140 are constructed of a rigid material, preferably polystyrene.

Referring again to FIG. 3, conveyor 160 selects a specimen disk 10 from Specimen Disk Entry Port 165 and aligns specimen disk 10 with Specimen Pipetting Station 170. Alternatively, specimen disk 10 may be manually loaded onto conveyor 160. Specimen Disk Entry Port 165 is a conventional object loading system. Conveyor 160 includes a conventional belt or chain conveying system or combination thereof.

At Specimen Pipetting Station 170, pipetting means 175 selects a disposable plastic pipette from Pipetting Tip Pickup Station 180, separately aspirates predetermined quantities of fluids from inner well 145, middle well 150 and outer well 155, respectively, injects the fluids into one reaction well 30 of specimen disk 10, then discards the disposable plastic pipette at Pipetting Tip Discard Station 185. This cycle is then repeated until all reaction wells 30 of specimen disk 10 have been loaded with samples.

By way of illustration but not limitation, the predetermined quantity of each fluid discussed above may be approximately 50 microliters. Pipetting means 175 includes a conventional pipetting system such as model RSP 9000 Robotic Sample Processor and model XL 3000 Series Multi-Channel Pump, both manufactured by CAVRO Scientific Instruments, Incorporated. Disposable plastic pipettes are conventional plastic pipettes, such as BIOHIT Proline™ tips, manufactured by BIOHIT OY, of Helsinki, Finland.

Conveyor 160 next transports specimen disk 10 to Additive Low Ionic Saline Solution Pipetting Station 190 at which a predetermined quantity of low ionic saline solution is quantitatively delivered by the previously described pipetting means into each reaction well 30 located in specimen disk 10. Low ionic saline solution enhances suppressed antibodies and facilitates antibody screening. By way of illustration but not limitation, the predetermined quantity of low ionic saline solution may be approximately 50 microliters.

Conveyor 160 next delivers specimen disk 10 to Initial Spin Station 195 at which specimen disk 10 is rapidly spun about axis 20 in order to centrifuge the solution held in each reaction well 30. In this manner, the red blood cells suspended in the blood specimen sample located in each reaction well 30 are compacted against each inner surface 56 of sample centrifugation barrier 55. Additionally, excess volume from solutions held in each reaction well 30 collects in waste chambers 60 leaving sufficient volume in each reaction well 30 to suspend the compacted cell mass above bottom viewing surface 90.

The rotation of specimen disk 10 is halted after approximately fifteen (15) seconds and specimen disk 10 is brought to rest. Specimen disk 10 is then agitated to dislodge the compacted cell mass from each inner surface 56 by rapidly rotating specimen disk 10 first in one direction then stopping the motion and rapidly rotating specimen disk 10 in the opposite direction. The dislodged compacted cell mass is then suspended in the remaining solution located above each bottom viewing surface 90. The spinning and agitation motion is accomplished through conventional centrifugation means.

Conveyor 160 next delivers specimen disk 10 to Incubation Station 200 at which the samples carried in specimen disk 10 are incubated at 37 degrees Celsius for a predetermined period of time. By way of example but not limitation, the incubation period may be about ten (10) minutes and is accomplished by heating Incubation Station 200 to 37 degrees Celsius by any conventional means, such as a resistance heater.

Specimen disk 10 is then delivered by conveyor 160 to Secondary Spin Station 205 at which specimen disk 10 is again centrifuged and agitated by previously described centrifugation means in order to further remove remaining excess fluid into waste chambers 60.

Specimen disk 10 is conveyed by conveyor 160 to First Microscopic Analysis Station 210 at which a digital image is created, displayed, stored and a histogram, i.e., printed record, is created for each sample held by specimen disk 10. Each reaction well 30 is successively positioned above a digital microscope and the compacted cell mass suspended in viewing area 85 is examined through viewing surface 90. The digital microscope creates, stores and prints a digital image of the suspended cell mass. The digital microscope is a conventional microscopic means such as the Bioquant™ BQ Meg IV Scientific Image Analysis System, manufactured by R & M Biometrics, Incorporated of Nashville, Tennessee.

Specimen disk 10 is next transported by conveyor 160 to Cell Wash Station 215 at which a predetermined quantity of solution, preferably composed of approximately 0.3% detergent and 0.9% saline, is injected by previously described pipetting means into each reaction well 30 in specimen disk 10 in order to wash the compacted cells. Specimen disk 10 is then centrifuged by previously described centrifugation means to remove excess fluid from reaction wells 30 into waste chambers 60. Specimen disk 10 is then agitated to dislodge and suspend material from the inner surface of sample centrifugation barrier 55 by the previously described method. This step is repeated two times.

Conveyor 160 then delivers specimen disk 10 to AHG Pipetting Station 230 at which a predetermined quantity of anti-human globulin solution is injected by previously described conventional means into each reaction well in specimen disk 10. The anti-human globulin solution further enhances agglutination reactions to the low ionic saline solution and also enhances suppressed antibodies.

Conveyor 160 next conveys specimen disk 10 to Final Spin Station 235. Specimen disk 10 is again rotated by previously described centrifugation means about axis 20 in order to remove excess fluid into waste chambers 60 in preparation for examining for enhanced antibody reactions.

Next, conveyor 160 transports specimen disk 10 to Second Microscopic Analysis Station 240 to determine the presence or absence of agglutination. At this station, a digitized image of each sample is created and displayed as previously described. Second Microscopic Analysis Station 240 may also permit storage and retrieval of the digitized image and other information, and may measure and locate cellular images. A cumulative record of the sample's data may then be printed by previously described conventional means.

Finally, conveyor 160 transports specimen disk 10 to Testing Disk Exit Port 245 where specimen disk 10 is cleaned, sanitized and prepared for reuse by soaking specimen disk 10 in sodium hypochlorite solution and rinsing with distilled, deionized water. Specimen disk 10 is stored in Specimen Disk Storage Area 250 where it is eventually retrieved and reused. Specimen Disk Storage Area 250 includes a conventional storage and delivery means.

The operations mentioned above are performed for all the successive samples located in specimen carousel 100.

It should be appreciated that this apparatus may be used with any immunoanalysis including, but not limited to, anti-body screening and identification by antibody reactions, donor/recipient compatibility cross matching and all other similar procedures. When performing these alternative testing procedures, the number of chambers in specimen carousel 100 may be varied to meet specific testing procedure requirements.

Although the present invention has been fully described in connection with the preferred embodiment thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed is:

1. A specimen disk for receiving a plurality of fluid specimens to be subjected to centrifugal separation and visual analyses comprising:

a generally circular disk member having a plurality of reaction wells radiating outwardly from a central bore;

means for accurately positioning said specimen disk during said centrifugal separation and visual analysis;

means for introducing fluids into each of said reaction wells;

a plurality of waste chambers each associated with a corresponding one of said plurality of reaction wells; and barrier means for trapping particulates when said disk is subjected to said centrifugal separation, said barrier means being positioned between each reaction chamber and a corresponding waste chamber and including an upstanding wall with inner and outer surfaces, an upper portion of said inner surface being substantially curved upward and inward toward said central bore in a generally C-shaped form in cross-section wherein each of said plurality of reaction wells includes a viewing area for containing a portion of said fluid specimen after said centrifugal separation and facilitating microscopic viewing of said fluid specimen therein.

2. The specimen disk according to claim 1, wherein said barrier means is located in each of said reaction wells between said viewing area and a corresponding waste chamber.

3. The specimen disk according to claim 1 wherein said viewing area is adjacent to said central bore of said disk member and said plurality of waste chambers are defined by said outer surfaces of said barrier means and along an outer periphery of said disk.

4. The specimen disk according to claim 3 further comprising:

a reaction well covering extending over all of said reaction wells, wherein said means for introducing fluids into each of said reaction wells comprises a plurality of covering holes in said reaction well covering.

5. The specimen disk according to claim 4, wherein 4 said plurality of reaction wells includes a reaction well bottom extending under all of said reaction wells, wherein said reaction well bottom forms a lower surface of said viewing area of each reaction well.

6. The specimen disk according to claim 5 wherein at least said inner surface is coated with a material to which said particulates in said fluid specimen do not strongly adhere.

* * * * *